United States Patent [19]

Mullins

[11] Patent Number: 4,701,549

[45] Date of Patent: Oct. 20, 1987

[54] ALKENYLAMINO CARBONYL CARBAMATES

[75] Inventor: Michael J. Mullins, Midland, Mich.

[73] Assignee: The Dow Chemical Company, Midland, Mich.

[21] Appl. No.: 878,142

[22] Filed: Jun. 25, 1986

Related U.S. Application Data

[60] Continuation-in-part of Ser. No. 817,709, Jan. 10, 1986, abandoned, which is a division of Ser. No. 682,528, Dec. 17, 1984, Pat. No. 4,572,804.

[51] Int. Cl.$^4$ .............................................. C07C 127/22
[52] U.S. Cl. ................................................... 560/159
[58] Field of Search ....................................... 560/159

Primary Examiner—Michael L. Shippen

[57] ABSTRACT

Prepare $\alpha,\beta$-unsaturated monoisocyanates by pyrolyzing $\alpha,\beta$-saturated geminal bis-carbamates.

20 Claims, No Drawings

ALKENYLAMINO CARBONYL CARBAMATES

CROSS-REFERENCE TO RELATED APPLICATION

This case is a continuation-in-part of application Ser. No. 817,709, filed Jan. 10, 1986, now abandoned, which is a Rule 60 Divisional of application Ser. No. 682,528, filed on Dec. 17, 1984, now U.S. Pat. No. 4,572,804.

BACKGROUND OF THE INVENTION

This invention relates to a method for the preparation of unsaturated isocyanates.

It is well-known that carbamates can be thermally cracked or pyrolyzed, to form the corresponding isocyanates, i.e., isocyanates which are identical to the starting molecule except for the conversion of the carbamate moiety to an isocyanate moiety. For example, see U.S. Pat. No. 2,409,712 and 2,713,591. U.S. Pat. No. 4,386,033 teaches the production of monoisocyanates from monocarbamates using an alcohol having a boiling point which is at least ±50° C. from the boiling point of the isocyanate produced. U.S. Pat. No. 3,919,279 discloses a method for producing saturated or unsaturated mono- or polyisocyanates via contacting the corresponding mono- or polycarbamates in certain solvents in the presence of a heavy metal at elevated temperatures. Dicarbamates yield diisocyanates using said method. Similarly, unsaturated carbamates yield unsaturated isocyanates via that method. U.S. Pat. No. 4,294,774 discloses a process for the preparation of an organic isocyanate by using an N,N-dialkyl aniline compound as a selectively-catalytic solvent. These patents are merely examples of known methods for the production of the corresponding isocyanate from the carbamate.

European patent application No. 55,359 teaches cleavage, at elevated temperature, of unsaturated monocarbamates to obtain the corresponding 1-alkenyl isocyanates. U.S. Pat. No. 4,388,246 discloses a similar thermal splitting reaction for di- and polycarbamates.

Heretofore, a method for producing an unsaturated monoisocyanate from a saturated geminal dicarbamate in a single step has not been disclosed.

SUMMARY OF THE INVENTION

The present invention is such a process, and involves pyrolyzing an $\alpha,\beta$-saturated geminal bis-carbamate to form an $\alpha,\beta$-unsaturated monoisocyanate. This process unexpectedly produces the unsaturated monoisocyanate from the saturated dicarbamate. Unsaturated monoisocyanates, which are difunctional in that they contain a reactive isocyanato moiety and a carbon-carbon double bond, are monomers for synthetic resins and plastics, and are intermediates for producing insecticides, dyes, pharmaceuticals, detergents, adhesives and bleaches. For example, the monomers can be polymerized by conventional free-radical polymerization techniques to form polymers which are useful as adhesives for bonding metal, wood and glass substrates.

DETAILED DESCRIPTION OF THE INVENTION

The $\alpha,\beta$-saturated geminal bis-carbamates employed as the starting material of the process of the present invention are characterized by having at least one carbon atom to which two carbamate moieties are attached, said carbon atom having a single bond to another atom, i.e., being $\alpha,\beta$-saturated. Preferred geminal bis-carbamates are represented by the formula

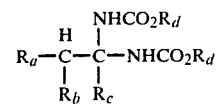

wherein $R_a$, $R_b$, $R_c$ and $R_d$ are independently aliphatic or aromatic moieties which can optionally contain halogen, N, O or S atoms; and $R_a$, $R_b$ and $R_c$ further independently can be H. Preferably, the $R_d$ moieties are identical to each other. In addition, it is preferred that $R_a$, $R_b$, $R_c$ and $R_d$ are independently lower alkyl of from 1 to about 4 carbon atoms; and $R_a$, $R_b$ and $R_c$ further independently can be H. Most preferably, $R_a$ and $R_b$ are hydrogen, $R_c$ is independently hydrogen, methyl or ethyl, and $R_d$ is methyl or ethyl.

Typically, the process is conducted by subjecting at least one geminal bis-carbamate to reaction conditions such that the pyrolysis occurs to yield the desired unsaturated monoisocyanate. In general, any combination of temperature and pressure at which the reaction occurs can be employed. The reaction temperature typically can be varied widely, however, a temperature of from about 100° C. to about 600° C. is commonly employed. Preferably, the temperature is from about 200° C. to about 400° C., with the most preferred temperature range being from about 250° C. to about 350° C. The reaction typically is performed at subatmospheric pressure, although atmospheric or superatmospheric pressures can be employed if desired. The reaction is commonly performed at from about 0 to about 1,000 mm Hg (0–133 KPa). Preferably, the reaction is conducted at from about 1 to about 760 mm Hg (0.133–101 KPa), and most preferably it is conducted at from about 2 to about 40 mm Hg (0.27–5.32 KPa).

Any reaction period which is sufficient for the conversion of the geminal bis-carbamate to the $\alpha,\beta$-unsaturated monoisocyanate can be employed. Typical reaction periods range from about 0.5 to about 5 seconds. The process is preferentially carried out in an atmosphere of an inert gas, such as nitrogen, in order to exclude from the reaction zone any gaseous oxygen or oxidizing agents which are well-known to oxidize organic carbamates or isocyanates.

In addition to the preferred method of adding the geminal bis-carbamate as a solid or molten liquid to the reaction zone, said bis-carbamate can optionally be employed as a solution with a non-reactive solvent or can be employed in the vapor phase. It is more preferred to feed the geminal bis-carbamate as a molten liquid. Examples of typical non-reactive solvents include aromatic hydrocarbons, such as toluene and xylene; chlorinated aromatic and aliphatic compounds, such as dichlorobenzene and methylene chloride; and aliphatic and aromatic ethers. When solutions are employed, they typically contain from about 5 to about 80 weight percent of the geminal bis-carbamate, and preferably contain from about 40 to about 50 percent of the bis-carbamate.

The pyrolysis can be conducted in any suitable apparatus, such as a tube of fused quartz, glass, metal, and the like. Preferably, the reaction zone is at least partially filled with a packing material. Typical packing materials include silica gel, clays, aluminas, zeolites, polymeric acids, and metal turnings. The packing material functions to promote an even distribution of heat, and preferably functions as a catalyst. Preferred packing materials include clays, silica gels, and alumina-silica gel combinations. Silica gel having a surface area of at least about 300 m²/g is most preferred.

When the geminal bis-carbamate is introduced to a reaction zone under reaction conditions as hereinbefore specified, an $\alpha,\beta$-unsaturated monoisocyanate will be formed. Preferred $\alpha,\beta$-unsaturated monoisocyanates are represented generally by the formula

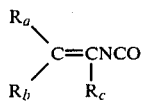

II wherein $R_a$, $R_b$ and $R_c$ are as defined hereinabove. An especially preferred product is isopropenyl isocyanate, e.g., $R_a$ and $R_b$ are H, and $R_c$ is methyl.

The pyrolysis process of the present invention typically produces by-products in addition to the $\alpha,\beta$-unsaturated monoisocyanate. These by-products include compounds represented by the following formulas: $R_dOH$, $R_dCO_2NH_2$, and

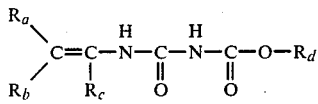

wherein $R_a$, $R_b$, $R_c$ and $R_d$ are as defined hereinabove. Compounds of the latter formula are believed to be novel, and are useful as monomers and as chemical intermediates in the production of biologically active compounds.

The preparation from aldehydes and carbamates of geminal bis-carbamates having a hydrogen atom on the geminal carbon is well-known. See, e.g., *J. Org. Chem.*, Vol. 10, pp. 145–8 and 483–97 (1945). Regardless of whether the geminal carbon has a hydrogen atom, the following method can be employed to prepare geminal bis-carbamates. Geminal bis-carbamates are readily prepared by contacting an $\alpha,\beta$-unsaturated ether with a carbamate in an inert solvent in the presence of an acid catalyst at a temperature of from about 0° C. or lower up to reflux temperature. Examples of this procedure are given infra.

SPECIFIC EMBODIMENTS

The following preparations and examples are given to illustrate the invention and should not be construed as limiting its scope.

PREPARATION 1

Synthesis of 2,2-N,N-bis-(ethyl carbamato)propane

A solution of ethyl carbamate (8.91 g, 100 mmoles) in 40 ml of methylene chloride is added to 15 mg of p-toluene sulfonic acid in a 100-ml round-bottom flask equipped with a stirring means. The mixture is cooled with ice water under a nitrogen atmosphere. Isopropenyl methyl ether (14 ml, density 0.765 g/ml, 131 mmoles) is added to the mixture over a period of about 20 minutes. The mixture is then allowed to stand for 20 minutes. The resulting colorless solution is washed twice using 10 ml of saturated NaHCO₃ solution each time, and then is washed twice using 10 ml of water each time. The washed solution is dried with magnesium sulfate, and is filtered and evaporated, leaving 10.56 g of white crystals having a melting point of 98.5° C. to 100° C. Recrystallization of the white crystals using toluene gives crystals having a melting point of 107° C. to 108° C. Spectral analyses (proton and carbon nuclear magnetic resonance, infrared and mass spectroscopy) are consistent with the assigned structure.

PREPARATION 2

Synthesis of 2,2-N,N-bis-(methyl carbamato)propane

The procedure of Preparation 1 is repeated with the following exceptions: ethyl carbamate is replaced with methyl carbamate (6.66 g, 88.7 mmoles); 35 ml of methylene chloride is employed; 38 mg of p-toluene sulfonic acid is employed; and 10.7 ml of isopropenyl methyl ether is employed. The initial white crystals weigh 7.99 g and have a melting point of 103° C. to 106° C. The white crystals are recrystallized from toluene to give crystals having a melting point of 122° C. to 123° C. Spectral analyses are consistent with the assigned structure.

EXAMPLE 1

Synthesis of isopropenyl isocyanate

A fused quartz tube having an inside diameter of about 12 mm, a length of about 200 mm, and a means for measuring the internal temperature thereof, is filled with coarse silica gel which was obtained from W. R. Grace and Company under the name Grade 59 Silica Gel. The tube is conditioned by heating it to 400° C. for 4 hours in a stream of nitrogen. The tube is then cooled to 300° C. and a vacuum of about 2 mm Hg (0.266 KPa) is applied. Then, 7.10 g of dimethyl isopropylidene dicarbamate (also called 2,2-N,N-bis-(methyl carbamato)propane) in solid form is introduced to the top of the vertically oriented tube over a period of about 25 minutes. During said period, the temperature is maintained between about 295° C. and about 305° C., and the pressure is maintained between about 2.5 to 3.0 mm Hg (333–400 Pa). The effluent from the tube is condensed in a flask cooled with dry ice. Methanol, isopropenyl isocyanate, and methyl carbamate are distilled off into a second flask at the same pressure. The isocyanate is isolated by washing the distillate three times with 2 ml of ice water. The undistilled material is predominantly 2-methoxy-2-N-(methyl carbamato)propane along with a small amount of methyl((isopropenylamino)carbonyl)-carbamate.

EXAMPLE 2

Synthesis of vinyl isocyanate

The procedure of Example 1 is repeated using dimethyl ethylidene dicarbamate, except that 3.49 g of the solid are introduced over a period of about 10 minutes. Analysis of the distillate by proton nuclear magnetic resonance and infrared spectra show the presence of methanol, methyl carbamate, and vinyl isocyanate. The undistilled material is a mixture of N-vinyl-O-methyl carbamate and methyl((ethenylamino)carbonyl)carbamate along with some methyl carbamate. The methyl(-(ethenylamino)carbonyl)carbamate and a N-vinyl-O-methyl carbamate are separated from methyl carbamate by distillation. This mixture of unsaturated monomers is then mixed with 0.1 percent of azobisisobutyronitrile and heated to a copolymerization temperature of 50° C. The resulting copolymer is heated to 100° C. at which temperature it is heat plastified and applied as a 3 mm thick layer to a steel panel. While the copolymer is still in a heat plastified state, a second steel panel is pressed against the heat plastified layer. The resulting laminate of the two steel panels and the intermediate bonding layer of the copolymer is cooled and tested for bond strength. The steel panels of the laminate cannot be readily separated.

The preceding examples illustrate the unexpected, one-step production of $\alpha,\beta$-unsaturated monoisocyanates via pyrolysis of $\alpha,\beta$-saturated dicarbamates.

What is claimed is:

1. A compound represented by the formula:

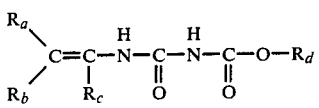

wherein $R_a$, $R_b$ and $R_c$ are independently H or alkyl, and $R_d$ is alkyl.

2. A compound of claim 1 wherein alkyl is lower alkyl.
3. A compound of claim 2 wherein $R_a$ and $R_b$ are H, $R_c$ is H, methyl or ethyl, and $R_d$ is methyl or ethyl.
4. A compound of claim 2 wherein $R_d$ is methyl.
5. A compound of claim 2 wherein $R_d$ is ethyl.
6. A compound of claim 1 wherein at least one of $R_a$, $R_b$ and $R_c$ is H or lower alkyl.
7. A compound of claim 6 wherein $R_c$ is methyl.
8. A compound of claim 6 wherein $R_c$ is ethyl.
9. A compound of claim 6 wherein $R_c$ is H.
10. A compound of claim 6 wherein $R_a$ and $R_b$ are H.
11. A compound of claim 10 wherein $R_c$ is methyl.
12. A compound of claim 10 wherein $R_c$ is ethyl.
13. A compound of claim 10 wherein $R_c$ is H.
14. A compound of claim 10 wherein $R_d$ is lower alkyl.
15. A compound of claim 14 wherein $R_d$ is ethyl.
16. A compound of claim 14 wherein $R_d$ is methyl.
17. A compound of claim 16 wherein $R_c$ is methyl.
18. A compound of claim 16 wherein $R_c$ is H.
19. Methyl((ethenylamino)carbonyl) carbamate.
20. Methyl((isopropenylamino)carbonyl)carbamate.

* * * * *